United States Patent [19]

Caupin et al.

[11] Patent Number: 5,504,142
[45] Date of Patent: Apr. 2, 1996

[54] DEVICE FOR CONTROLLING INSECTS

[75] Inventors: Henri-Jean Caupin, Versailles; Roland Leroux, Chaville; Michel Guillon, Pau, all of France

[73] Assignee: Elf Atochem S.A., France

[21] Appl. No.: 434,489

[22] Filed: May 4, 1995

[30] Foreign Application Priority Data

May 6, 1994 [FR] France .................. 94 05685

[51] Int. Cl.$^6$ ............ A01N 25/26; A01N 25/34
[52] U.S. Cl. ............ 524/548; 524/601; 424/405; 424/408
[58] Field of Search .................. 424/405, 408; 524/601, 548

[56] References Cited

U.S. PATENT DOCUMENTS

| | | | |
|---|---|---|---|
| 4,115,475 | 9/1978 | Foy et al. | 260/857 PE |
| 4,195,015 | 3/1980 | Deleens et al. | 260/45.75 C |
| 4,331,786 | 5/1982 | Foy et al. | 525/408 |
| 4,734,281 | 3/1988 | Yamamoto et al. | 424/408 |
| 4,839,441 | 6/1989 | Cuzin et al. | 528/328 |
| 4,864,014 | 9/1989 | Cuzin et al. | 528/279 |
| 4,908,208 | 3/1990 | Lee et al. | 424/409 |
| 4,981,689 | 1/1991 | Shikinami et al. | 424/409 |
| 4,984,376 | 1/1991 | Walter et al. | 36/30 R |
| 4,988,740 | 1/1991 | Walter et al. | 521/138 |
| 5,008,115 | 4/1991 | Lee et al. | 424/486 |
| 5,130,171 | 7/1992 | Prud'Homme et al. | 427/213.36 |
| 5,142,817 | 9/1992 | Rolf | 47/24 |
| 5,310,557 | 5/1994 | Brandt et al. | 424/411 |

FOREIGN PATENT DOCUMENTS

| | | |
|---|---|---|
| 28256/92 | 5/1993 | Australia. |
| 0367140A3 | 5/1990 | European Pat. Off.. |
| 0367140A2 | 5/1990 | European Pat. Off.. |
| 0542081A1 | 5/1993 | European Pat. Off.. |
| 2579983A1 | 10/1986 | France. |
| 3611137A1 | 10/1986 | Germany. |

OTHER PUBLICATIONS

Sanyo, Derwent WPI, Acc. No. 78–24032A/13, abstract of JP 53015423 (Feb. 1978).
Kagaku, Derwent WPI, Acc. No. 81–78581D/43, abstract of JP 56115377 (Sep. 1981).
Otsuka, Derwent WPI, Acc. No. 82–84503E/40, abstract of JP 57139005 (Aug. 1982).
Takiron, Derwent WPI, Acc. No. 88–320105/45, abstract of JP 63238001 (Oct. 1988).

*Primary Examiner*—W. Robinson H. Clark
*Attorney, Agent, or Firm*—Pennie & Edmonds

[57] ABSTRACT

The present invention relates to a mixture comprising (i) a thermoplastic elastomer, (ii) at least one chemical mediator acting on the behavior of insects and acarids and chosen from pheromones, kairomones, or allomones, and optionally, (iii) undecylenic acid or derivatives thereof. The invention is particularly useful for treating crops against insects and acarids.

12 Claims, No Drawings

DEVICE FOR CONTROLLING INSECTS

FIELD OF THE INVENTION

The present invention relates to a device for controlling insects by the slow diffusion of chemical mediators such as pheromones. More particularly, the present invention relates to thermoplastic resin devices that contain the chemical mediators and that diffuse them slowly into the atmosphere.

BACKGROUND OF THE INVENTION

The protection of crops against insects has involved the use of organic synthesis products with a wide spectrum of action which are intended to kill insects in a non-specific manner. The amounts required are large. Many of these products are hazardous to the environment and some, such as DDT, have been banned.

Insects may also be controlled by chemical mediators which regulate insect-insect relationships or plant-insect relationships. Among such chemical mediators are pheromones, kairomones, and allomones. Pheromones are chemical substances that are use for communication between individual organisms of the same species. Allomones cause a reaction in another species which is favorable to the organism secreting the substance. Kairomones are either nonadaptive or detrimental to the organisms producing them.

In contrast with conventional products for the destruction of insects, these mediators are used in very low amounts, for example two or three treatments of 10 to 20 grams per hectare, or continuous diffusion of a few milligrains per hectare and per hour for one or more months.

U.S. Pat. No. 4,734,281 describes a method for diffusing insect sex pheromones into the air. These pheromones modify behavior by preventing the reproduction of certain insects. These pheromones, which are in liquid form, are placed in polyethylene bags. The pheromones diffuse through the bag and become dispersed into the air. Example 1 of the patent shows polyethylene tubes 0.8 mm in internal diameter, 1.4 mm in outside diameter, and 200 mm in length that are filled with 80 mg of a mixture of two pheromones. The ends of the tubes are then sealed. At 30° C. in a stream of air of 0.5 m/s, a diffusion of 0.4 and 0.5 mg per day of each pheromone is observed.

U.S. Pat. No. 5,142,817 describes sheets or strips formed of a sheet of water-insoluble polymer adhesively bonded to a sheet of a hydrophilic matrix. This matrix may be made of cellulose fibers, polyester, polyacetate, polyvinyl alcohol, or polyoxyethylene glycol. This matrix contains a plasticizer such as polyoxyethylene glycol or a sorbitol solution and also a biologically active product. These strips serve to envelop trees. The biologically active product is released by a humid atmosphere and serves to protect the trees.

EP 367,140 describes copolymers of ethylene and of vinyl acetate containing 5 to 30% of p-menthane-3,8-diol, an insect repellent. Granules may be made therefrom, which are placed on the roots of trees or on the collars of domestic animals.

Japanese Application 87 JP-069396, published as KOKAI JP 63238001, describes strips for winding around the branches of trees, consisting of a photodegradable sheet covered with a mixture of an insecticide and a polyether urethane or polyester urethane prepolymer.

Japanese Application 81 JP-024042, published as KOKAI JP 57 139005, describes compositions of pheromones and of a binder containing 4 to 20% of pheromones. The binder is silicone or SBR rubber. A solvent such as methylene chloride, benzene, an alcohol, etc. and fillers such as cellulose, silica, active carbon, or carbonate are also used. The product is in paste form.

Patent FR 2,579,983 describes perfume-filled polymers which diffuse these perfumes into the ambient air.

The prior art shows the diffusion of liquid pheromones through polyethylene containers. The preparation of these polyethylene tubes, their filling with pheromones, the sealing and then the transportation and the positioning in the crops is complicated.

The diffusion of pheromones from pastes filled with between 4 and 20% of pheromones requires the transportation and the positioning of considerable amounts of fillers. In addition, the diffusion from a paste is not as uniform as the diffusion of a liquid through a wall.

SUMMARY OF THE INVENTION

Materials have now been found which can diffuse pheromones uniformly for long periods, and which could contain a large reserve of pheromones. These materials may be in granule, bead, stick, etc. form. In addition, it is very easy to impregnate them with pheromones.

The present invention provides a composition of matter comprising: a thermoplastic elastomer selected from the group consisting of polyether polyesters, copolyetherimide esters, and polyether polyamides; at least one chemical mediator acting on the behavior of insects and acarids and selected from the group consisting of pheromones, kairomones, and allomones; and an undecylenic acid component selected from the group consisting of undecylenic acid and $C_1$-alkyl to $C_6$-alkyl esters thereof.

Another aspect of the present invention is an article of manufacture comprising that composition of matter in the form of granules or sticks.

The present invention also provides a method for the preventive or curative protection of a site against insects and acarids which feed on crops which comprises applying onto the site a composition or an article as described above.

DESCRIPTION OF THE PREFERRED EMBODIMENTS

The present invention contemplates a mixture comprising (i) a thermoplastic elastomer having polyether units, (ii) at least one chemical mediator acting on the behavior of insects and acarids and chosen from pheromones, kairomones, or allomones, and (iii) undecylenic acid or derivatives thereof. The thermoplastic elastomer The thermoplastic elastomer may comprise polyether units and polyester units. They are, for example, polyether blocks and polyester blocks. These products are known under the name of elastomeric polyesters and are thermoplastic.

The polyethers are, for example, polyethylene glycol, polypropylene glycol, or polytetramethylene glycol. The molar mass Mn of these polyethers may be between 250 and 6000. These polyethers condense with at least one dicarboxylic acid to form the flexible segments of the elastomeric polyesters.

The polyester blocks result, for example, from the condensation of at least one diol with at least one dicarboxylic acid. The diol may be glycol, propanediol, or butanediol. The diacid may be terephthalic acid. These blocks form the hard segments of the elastomeric polyester.

The hard segments may comprise several units resulting from the action of a diol on a diacid. The flexible segments may comprise several units resulting from the action of the polyether on a diacid. The hard segments and the flexible segments are attached together by ester bonds.

Such elastomeric polyesters are described in U.S. Pat. Nos. 4,984,376 and 4,988,740, the disclosures of which are herein expressly incorporated by reference.

The thermoplastic elastomers according to the present invention may also be copolyetherimide esters.

The flexible segments are formed by the reaction of polyether diamines with tricarboxylic compounds or carboxylic anhydrides containing a carboxylic group such as, for example, trimellitic anhydride. The polyether diamines used have an average molar mass of 600 to 12000. These polyether diamines may themselves be derived from polyethylene glycol, polypropylene glycol or polytetramethylene glycol.

The polyester blocks forming the segments in copolyetherimide esters result, for example, from the condensation of at least one diol with at least one dicarboxylic acid. The diol may be glycol, propanediol, or butanediol. The diacid may be terephthalic acid.

Such copolyetherimide esters are likewise described in U.S. Pat. Nos. 4,984,376 and 4,988,740, the disclosures of which are herein expressly incorporated by reference at this point also.

The elastomers most frequently used are those comprising polyamide blocks and polyether blocks. The polyamide blocks may originate either from the condensation of a lactam or of an $\alpha,\omega$-amino acid or from the reaction of a diacid and a diamine.

These polyamide blocks may be prepared in the presence of a diacid. Polyamide blocks containing carboxylic acid ends are obtained. The molar mass Mn of the polyamide blocks may be between 600 and 5000.

The polyethers are, for example, polyethylene glycol, polypropylene glycol or polytetramethylene glycol of molar mass Mn between 250 and 6000, and several polyethers may be linked together, for example by diacids in the case of polyether diols.

As regards the thermoplastic elastomers which comprise polyether units and amide units, they may be distributed in a random or ordered manner. The amide units may be isolated or grouped in oligomers originating from the reaction of a diamine with a diacid or from the condensation of an $\alpha,\omega$-aminocarboxylic acid.

It would not be departing from the scope of the invention to use other elastomers containing polyamide blocks and polyether blocks. These products may be prepared by reaction of lactam or $\alpha,\omega$-amino acid of diacid and of polyether diol or polyether diamine. It is also possible to condense polyamide blocks containing amino ends with polyether diacids, and to condense polyamide blocks containing acid ends with polyether diamines.

All these products are described in U.S. Pat. Nos. 4,331, 786, 4,115,475, 4,195,015, 4,839,441, and 4,864,014, the disclosures of which are herein expressly incorporated by reference.

The chemical mediator

The chemical mediators are known products. For instance, 4-methyl-3-heptanone is a synthetic pheromone that disrupts the mating behavior of insect pests. The compound phoromone, in chemical nomenclature 7-ethyl-5-methyl-6,8 -dioxabicyclo-[3.2.1]-octane, is a product excreted by bark beetles that acts as a sex attractant and is used in the protection of forest timber. Among the pheromones that are most preferred in accordance with the present invention are those of CHILO SUPPRESSALIS, one of the creatures which devastates rice, and of the maize stalk borer. The CHILO SUPPRESSALIS pheromone is a mixture of hexadecenol, hexadecenal, and octadecenal. The maize stalk borer pheromone is a mixture of hexadecenol, hexadecenal, hexadecenyl acetate, and dodecanyl acetate.

The mixture of the invention may contain up to 90 parts of chemical mediator per 100 parts of elastomer.

The undecylenic acid component

The term undecylenic acid derivatives refers both to the water-soluble derivatives and to the lipid-soluble derivatives. Such derivatives are, for example, $C_1$ to $C_6$ alkyl esters, and advantageously $C_1$ to $C_3$ alkyl esters such as the methyl, ethyl, or isopropyl esters. Methyl undecylenate is preferably used.

The composition of the invention may contain up to 90 parts of undecylenic acid or derivatives thereof per 100 parts of elastomer.

The device

The mixture of the invention may be in the form of granules, beads, or sticks. In general, it may be in any form which enables it to be transported and to be dispersed or arranged easily in crops or plantations.

The mixing of thermoplastic elastomer and of chemical mediator may take place by quenching of the elastomer in the mediator or in a solution containing the mediator. This solution may be based on an alcohol.

Alternatively, undecylenic acid or derivatives thereof may be incorporated into the elastomer, and the process then performed as above.

However, preferably, a solution (the solution hereinbelow) of chemical mediator in undecylenic acid or derivatives thereof is prepared and then incorporated into the elastomer. The process for the incorporation of an undecylenic acid or derivative thereof into an elastomer is described in Patent FR 2,697,848. It may be summarized as follows: The solution may be mixed with elastomer granules; it is thus possible to prepare a main mixture which is then incorporated into the elastomer according to the standard techniques for plastics. It is also possible to dilute the solution in an alcohol and then to mix with the elastomer. Swelling of the elastomer is observed, the alcohol evaporates, and the product of the invention remains, namely the elastomer, the chemical mediator, and the undecylenic acid or derivatives thereof. A saturated $C_1$ to $C_6$ alcohol is preferably used.

EXAMPLES

The following non-limiting Examples illustrate the invention.

Example 1

| | |
|---|---|
| Pheromone | 3 g |
| Methyl undecylenate | 27 g |
| Elastomer | 100 g |

The mixture is in the form of sticks 20 mm in diameter and 150 nm in length.

The elastomer is formed of polyamide blocks containing carboxylic acid ends connected to polyether blocks containing OH ends by means of ester functions. The polyamide blocks are derived from lactam 12 and the polyether blocks are from polytetramethylene glycol.

The pheromone is that from CHILO SUPPRESSALIS, one of the creatures which devastates rice. This pheromone is 82 weight-percent Z9-hexadecenol, 9.8 weight-percent Z13-octadecenal, and 8.2 weight-percent Z11-hexadecenal.

The sticks were placed in tunnels flushed with air, and the amounts of pheromones diffused were measured. The amounts diffused were measured for 120 days; the values were constant.

EXAMPLE 2

Example 1 was reproduced with another pheromone, that of the maize stalk borer. This pheromone is 69 weight-percent Z11-hexadecenal, 15 weight-percent n-dodecanyl acetate, 8 weight-percent Z11-hexadecenol, and 8 weight-percent Z11-hexadecenyl acetate.

The same results were obtained.

It was noted that no modification of the chemical structure of the pheromones occurred during the course of these diffusion tests. This is contrary to the experience when temperature is used to introduce pheromones on carriers. These pheromones are unstable and polymerize quickly above 10° C.

Although this invention has been described and illustrated with reference to specific materials, those skilled in the art are taught broader principles by the present disclosure of the invention. Accordingly, the spirit and scope of the invention patented are reflected in the appended claims.

What is claimed is:

1. A composition comprising: a thermoplastic elastomer selected from the group consisting of polyether polyesters, copolyetherimide esters, and polyether polyamides; at least one chemical mediator acting on the behavior of insects and acarids and selected from the group consisting of pheromones, kairomones, and allomones; and an undecylenic acid component selected from the group consisting of undecylenic acid and $C_1$-alkyl to $C_6$-alkyl esters thereof.

2. The composition according to claim 1, wherein the elastomer comprises polyamide blocks and polyether blocks.

3. The composition according to claim 1, wherein the chemical mediator is a pheromone.

4. The composition according to claim 3, wherein the pheromone comprises a member selected from the group consisting of Z11-hexadecenal, Z9-hexadecenol, Z13-octadecenal, n-dodecanyl acetate, Z11-hexadecenol, Z11-hexadecenyl acetate, and mixtures thereof.

5. The composition according to claim 1, wherein the undecylenic acid component is methyl undecylenate.

6. An article of manufacture comprising a composition according to claim 1 in the form of granules or sticks.

7. An article of manufacture comprising a composition according to claim 2 in the form of granules or sticks.

8. An article of manufacture comprising a composition according to claim 3 in the form of granules or sticks.

9. An article of manufacture comprising a composition according to claim 4 in the form of granules or sticks.

10. An article of manufacture comprising a composition according to claim 5 in the form of granules or sticks.

11. A method for the preventive or curative protection of a site against insects and acarids which feed on crops which comprises applying onto the site a composition according to one of claims 1 to 5 or an article of manufacture according to one of claims 6–10.

12. The method of claim 11 wherein said application is conducted at or below a temperature of 10° C.

* * * * *